(12) United States Patent
Pigg et al.

(10) Patent No.: US 10,953,127 B2
(45) Date of Patent: Mar. 23, 2021

(54) ABSORBENT FOAM WOUND DRESSING MATERIALS

(75) Inventors: William Pigg, York (GB); Michelle Del Bono, Barnoldswick (GB); Paul Howard Lowing, Keighley (GB)

(73) Assignee: KCI USA, INC., San Antonio, TX (US)

( * ) Notice: Subject to any disclaimer, the term of this patent is extended or adjusted under 35 U.S.C. 154(b) by 0 days.

(21) Appl. No.: 13/146,553

(22) PCT Filed: Feb. 3, 2010

(86) PCT No.: PCT/GB2010/000190
§ 371 (c)(1),
(2), (4) Date: Dec. 12, 2011

(87) PCT Pub. No.: WO2010/089546
PCT Pub. Date: Aug. 12, 2010

(65) Prior Publication Data
US 2012/0078154 A1    Mar. 29, 2012

(30) Foreign Application Priority Data

Feb. 4, 2009 (GB) .................................. 0901865.6

(51) Int. Cl.
*A61L 15/42* (2006.01)
*A61L 15/22* (2006.01)
(52) U.S. Cl.
CPC ........... *A61L 15/425* (2013.01); *A61L 15/225* (2013.01)

(58) Field of Classification Search
CPC .. A61L 15/425; A61F 13/00042; A61F 13/00; A61F 13/00021; A61F 2013/0074; A61M 2205/0266
(Continued)

(56) References Cited

U.S. PATENT DOCUMENTS 3,369,547 A    2/1968 Sack et al.
4,182,649 A    1/1980 Isgur et al.
(Continued)

FOREIGN PATENT DOCUMENTS

EP    1 600 096 A2    11/2005
EP    1600096 A2 *    11/2005 ............. A47L 13/16
(Continued)

OTHER PUBLICATIONS

Search Report issued by the UKIPO in priority Application No. GB 0901865.6.
(Continued)

*Primary Examiner* — Rachael E Bredefeld
*Assistant Examiner* — Caitlin A Carreiro
(74) *Attorney, Agent, or Firm* — Foley & Lardner LLP

(57) ABSTRACT

A wound dressing material comprising a solid substrate having interstitial spaces therein, wherein said substrate is a hydrophilic open-cell foam material, and wherein said interstitial spaces are at least partially filled by a hydrophilic polyurethane foam different from said substrate foam material. Also provided is a method of making a porous wound dressing material comprising the steps of: providing a substrate of a solid hydrophilic first foam material; applying a fluid or gel polyurethane foam prepolymer mixture to at least one surface of said solid substrate; and curing said prepolymer in contact with said solid substrate.

20 Claims, 2 Drawing Sheets

(58) Field of Classification Search
USPC .............. 602/41–43, 46; 424/445; 428/304.4
See application file for complete search history.

(56) References Cited

U.S. PATENT DOCUMENTS

| | | | |
|---|---|---|---|
| 4,961,985 A | 10/1990 | Henn et al. | |
| 5,135,472 A * | 8/1992 | Hermann | .......... A61F 13/00008 |
| | | | 424/446 |
| 6,399,854 B1 * | 6/2002 | Vartiainen | ............. A61F 13/531 |
| | | | 264/45.3 |
| 6,617,014 B1 * | 9/2003 | Thomson | .................. B32B 5/18 |
| | | | 428/304.4 |
| 2005/0148920 A1 * | 7/2005 | Addison | ........... A61F 13/00995 |
| | | | 602/46 |

FOREIGN PATENT DOCUMENTS

| | | | |
|---|---|---|---|
| EP | 1600096 A2 * | 11/2005 | ............. A47L 13/16 |
| GB | 2 357 286 A | 6/2001 | |
| GB | 2396109 | 6/2004 | |
| WO | 02/45761 | 6/2002 | |

OTHER PUBLICATIONS

The International Search Report from International Application No. PCT/GB2010/000190.

* cited by examiner

ABSORBENT FOAM WOUND DRESSING MATERIALS

CROSS-REFERENCE TO RELATED APPLICATION

The present application claims priority to International Application No. PCT/GB2010/000190, filed 3 Feb. 2010, which claims priority to United Kingdom Application No. 0901865.6, filed 4 Feb. 2009, all of which are hereby incorporated by reference in their entireties.

FIELD OF THE INVENTION

This invention relates to wound dressing materials, and more particularly to improved absorbent foam materials. The invention also relates to a wound dressing having a wound-contacting layer formed from such a material, and to methods of making such materials.

BACKGROUND OF THE INVENTION

Polyurethane foams have been proposed for a number of medicinal uses. The foams are prepared by reacting particular diisocyanates or isocyanate-capped prepolymers with suitable chain extending compounds having amine and/or alcohol multiple functionality. Chain terminating compounds such as mono-amines or monohydric alcohols may be included in the reaction mixture. Water may be included in the reaction mixture, since it reacts with isocyanate to liberate carbon dioxide for foaming the mixture. The resulting foams are absorbent, hydrophilic, and may be medically acceptable for use in wound dressings and the like.

EP-A-0541391 describes a method of forming a polyurethane foam suitable for use as a wound-contacting layer, the method comprising mixing 1 part by weight of an isocyanate-capped prepolymer having a relatively low isocyanate content of from 0.5 to 1.2 meq NCO groups/g with from 0.4 to 1.0 parts by weight of water in the presence of from 0.05 to 0.4 parts by weight of a C1 to C3 monohydric alcohol, and then drying the product. The use of a relatively small amount of water produces an initial reaction mixture of much higher initial viscosity. Carbon dioxide formed by hydrolysis of isocyanate end groups is therefore trapped, producing a foamed hydrogel. For use as a wound-contact layer, topical medicaments and antiseptics, such as silver sulfadiazine, povidone iodine, chlorhexidine acetate and chlorhexidine gluconate, as well as other therapeutically useful additives such as polypeptide growth factors and enzymes may be incorporated into one or more of the components used to make the foaming mixture. These products manufactured by Johnson & Johnson have achieved commercial success under the Registered Trade Mark TIELLE.

U.S. Pat. No. 5,135,472 describes wound dressing materials formed by impregnating a polyurethane foam prepolymer mixture into a fibrous substrate, such as a cotton gauze. The polyurethane coating reduces the tendency of the gauze to shed fibers into a wound.

U.S. Pat. No. 3,369,547 describes laminating a polyurethane foam layer to a non-woven fibrous web to form an integral structure.

EP-A-1600096 describes absorbent sheet materials formed from nonwoven fibrous substrates incorporating distributed foam particles.

U.S. Pat. No. 4,182,649 describes composite polyurethane foam sheet prepared by mixing fibres with a liquid polyurethane foam prepolymer.

A need exists for improvements to the above polyurethane foam wound contacting materials. In particular, it would be desirable to be able to optimize the liquid absorbency of such materials for different applications. It would also be desirable to increase the mechanical strength of the materials for certain applications. It would also be desirable to provide dressings having increased thickness at moderate cost. It would also be desirable to provide dressings having greater elasticity and/or compressibility.

U.S. Pat. No. 6,617,014 describes impregnating a liquid polyurethane foam prepolymer into a hydrophobic foam support having an open-celled structure. The resulting materials are used for the treatment of aqueous liquids.

SUMMARY OF THE INVENTION

In a first aspect, the present invention provides a wound dressing material comprising a solid substrate having interstitial spaces therein, wherein said substrate is a hydrophilic open-cell foam material, and wherein said interstitial spaces are at least partially filled by a hydrophilic polyurethane foam different from said substrate foam material.

In a further aspect, the present invention provides a wound dressing comprising a wound dressing material according to the present invention.

In a further aspect, the present invention provides a method of making a porous wound dressing material comprising the steps of: providing a sheet of a solid substrate having interstitial spaces therein, wherein said substrate is a hydrophilic open-cell foam material; applying a fluid polyurethane foam prepolymer mixture to at least one surface of said solid substrate; and curing said prepolymer in contact with said solid substrate.

The solid substrate provides cushioning, mechanical support and mechanical strength to the hydrophilic polyurethane foam, and also provides a reservoir for absorbed liquid so that the absorbency of the material can readily be increased by increasing the thickness and/or porosity of the substrate without increasing the amount of the relatively expensive hydrophilic polyurethane foam.

DETAILED DESCRIPTION OF THE INVENTION

The solid substrate is formed from a hydrophilic open-cellular foam material, suitably a material that does not swell or dissolve significantly in water or wound fluid. The solid substrate provides increased liquid absorbency, thickness, and mechanical support to the hydrogel foam. The solid substrate is porous, with a plurality of interstitial spaces that are connected to provide pathways for liquid uptake. Suitably, the porosity (void volume) of the substrate is at least about 25%, for example at least about 50%. Suitably, the solid substrate is in the form of a sheet, for example a sheet having an uncompressed thickness of from about 0.2 mm to about 15 mm, for example from about 0.5 mm to about 5 mm.

The substrate foam is a medically acceptable material, that is to say a material approved for use in a wound dressing. Suitable open-cell foams include polyurethane foams, carboxylated butadiene-styrene rubber, polyacrylate, polyvinylic or cellulosic foams. Where necessary, the foam material has been treated to render it hydrophilic. Suitably, the open cell foam comprises a polyurethane substrate foam (having porosity and composition different from the hydrophilic polyurethane foam in the interstices), and more suitably it comprises at least 50% by weight of one or more polyurethanes, for example at least 75% by weight thereof.

The substrate foam is hydrophilic. That is to say, it absorbs water even in the absence of the interstitial second foam. Suitably, the uncompressed substrate foam will absorb at least 100% by weight of saline solution at 25° C. based on the weight of the dry substrate foam, more suitably at least about 200%, for example at least about 300% by weight of water in the absence of the interstitial second foam, as measured by the method of Procedure 1 below. The substrate foam thereby provides a reservoir and/or additional absorbency at lower cost than could be achieved by the use of a thicker TIELLE layer.

The pores of the substrate foam are suitably larger than the pores of the interstitial foam. Suitably, the linear cell count of the substrate foam is from about 5 to about 30 pores per cm, more suitably from about 10 to about 25 pores per cm. The density of the substrate foam (before addition of the hydrophilic foam second material) is suitably from about 10 to about 50 kg/m$^3$, for example from about 20 to about 40 kg/m$^3$.

The substrate foam is suitably compressible and elastic, so that it can conform readily to the wound bed and apply gentle pressure to the wound bed to improve wound healing. Suitably, the substrate foam can be compressed to about 50% of its uncompressed thickness and substantially recover to its original shape (i.e. compression set less than about 10% after 50% compression). Suitably, the substrate foam has an elongation at break greater than about 100%.

The support foam provides mechanical strength to the dressing materials of the invention. Accordingly, the support foam suitably has both wet and dry strengths (as determined below) greater than those of the interstitial polyurethane foam. Suitably, the tensile strength of the support foam is greater than about 50 kPa, for example greater than about 100 kPa.

The absorbent materials according to the invention are characterized by the presence of a hydrophilic polyurethane second foam at least partially filling the interstices of the solid support foam. The polyurethane foam is hydrophilic and swells with absorption of moisture to provide a wound-friendly surface to the dressing similar to that achieved with the commercial TIELLE dressings. Suitably, the polyurethane second foam is more hydrophilic than the substrate foam, that is to say it absorbs more saline at 25° C. when tested according to Procedure 1 below than the substrate foam. Typical saline uptake is in the range 400% to 800% of the dry weight of the second foam material. Typically, the polyurethane second foam absorbs water to form a moist, soft hydrogel foam layer.

Suitably, the porous wound dressing material according to the invention comprises from about 10 wt % to about 90 wt. % of said hydrophilic polyurethane second foam, based on the total weight of the material, for example from about 25 wt. % to about 75 wt % of the hydrophilic polymer second foam.

In certain embodiments, the hydrophilic polyurethane second foam may be distributed substantially uniformly through the solid substrate foam. In other embodiments, the hydrophilic polyurethane second foam is applied to one side only of said substrate foam. In these embodiments, the polyurethane foam penetrates into the interstices on one side of the substrate foam, which is the wound-facing side in use. The said surface in these embodiments may consist essentially of the hydrophilic second foam material, i.e. may be substantially completely coated with the hydrophilic foam material, in order to present a more wound friendly surface.

Suitably, the material according to the present invention comprises less than 10% water prior to use as an absorbent, more suitably less than 5% water and more suitably it contains less than 2% of water before use.

Suitably, the material according to the present invention is in the form of a sheet, for example a sheet having an uncompressed thickness of from about 0.2 mm to about 15 mm, for example from about 0.5 mm to about 5 mm.

Materials according to the invention typically have a density of from about 0.30 g/cm$^3$ to about 0.50 g/cm$^3$, for example from about 0.35 g/cm$^3$ to about 0.45 g/cm$^3$.

Depending on the proportions of other additives, the materials according to the invention suitably have an absorbency of at least 3 g saline/g, suitably at least 5 g/g, and more suitably from 8 to 20 g/g, as measured according to Procedure 1 below. The materials are thus highly absorbent, yet strong.

Suitably, the materials according to the present invention are sterile. They may be packaged in a microorganism-impermeable container.

The hydrophilic polyurethane second foam materials are formed by reacting particular diisocyanates or isocyanate-capped prepolymers with suitable chain extending compounds having amine and/or alcohol multiple functionality. Chain terminating compounds such as mono-amines or monohydric alcohols may be included in the reaction mixture. Water may be included in the reaction mixture, since it reacts with isocyanate to liberate carbon dioxide for foaming the mixture. Further details of the components of the hydrophilic polyurethane foam materials are given below.

The hydrophilic polyurethane second foams used in the materials of the invention also have the property of swelling and expanding when water is absorbed. This is particularly advantageous in a wound contact layer, because the swelling of the foam causes it to move inwards towards the wound bed, thus filling the wound cavity. This encourages the wound to heal from the base upwards and outwards, and it discourages epithelialization over the wound surface before the bed has been filled with granulation tissue. However, the foam is suitably highly cross-linked and substantially insoluble in water. The hydrophilic polyurethane foam may be open-cell or closed-cell.

The degree of swelling of the hydrophilic polyurethane second foams on complete saturation with an aqueous medium is typically at least 100% (expressed in terms of increase in volume), and suitably at least 200%. Preferred foams swell by 400 to 800%. Despite this high degree of swelling, however, the foams retain their integrity even after absorption of large quantities of water. Typically, the cells of the hydrophilic polyurethane second foams have an average diameter in the range 0.1 to 0.6 mm.

Suitably, the basis weight of the hydrophilic polyurethane second foam in the materials of the present invention is from 0.2 to 1.5 kg/m$^2$, more suitably 0.5 to 1.0 kg/m$^2$.

In a further aspect, the present invention provides a wound dressing comprising a wound dressing material according to the invention.

The wound dressing is suitably in sheet form and comprises a sheet (layer) of the material according to the invention. However, alternative shapes such as cavity filling wounds are also envisaged. The layer according to the invention would normally be the wound contacting layer in use, but in some embodiments it could be separated from the wound by a liquid-permeable top sheet. Suitably, the area of the sheet of material according to the invention is from about 1 cm$^2$ to about 400 cm$^2$, more suitably from about 4 cm$^2$ to about 100 cm$^2$.

Suitably, the wound dressing further comprises a backing sheet extending over the absorbent layer according to the invention, opposite to the wound facing side of the said absorbent layer. Suitably, the backing sheet is larger than the layer according to the invention such that a marginal region of width 1 mm to 50 mm, suitably 5 mm to 20 mm extends around the said layer to form a so-called island dressing. In such cases, the backing sheet is suitably coated with a pressure sensitive medical grade adhesive in at least its marginal region.

Suitably, the backing sheet is substantially liquid-impermeable. The backing sheet is suitably semipermeable. That is to say, the backing sheet is suitably permeable to water vapour, but not permeable to liquid water or wound exudate. Suitably, the backing sheet is also microorganism-impermeable. Suitable continuous conformable backing sheets will suitably have a moisture vapor transmission rate (MVTR) of the backing sheet alone of 300 to 5000 $g/m^2/24$ hrs, suitably 500 to 2000 $g/m^2/24$ hrs at 37.5° C. at 100% to 10% relative humidity difference. The backing sheet thickness is suitably in the range of 10 to 1000 micrometers, more suitably 100 to 500 micrometers. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Suitably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is suitably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is suitably 20 to 250 $g/m^2$, and more suitably 50 to 150 $g/m^2$. Polyurethane-based pressure sensitive adhesives are preferred.

Further layers of a multilayer absorbent article may be built up between the layer according to the present invention and the protective sheet. For example, these layers may comprise one or more further absorbent layers between the layer according to the invention and the protective sheet, especially if the dressing is for use on exuding wounds. The optional further absorbent layer may be any of the layers conventionally used for absorbing wound fluids, serum or blood in the wound healing art, including gauzes, nonwoven fabrics, superabsorbents, hydrogels and mixtures thereof. Suitably, the absorbent layer comprises a layer of absorbent foam, such as an open celled hydrophilic polyurethane foam prepared in accordance with EP-A-0541391. In other embodiments, the absorbent layer may be a nonwoven fibrous web, for example a carded web of viscose staple fibers. The basis weight of the absorbent layer may be in the range of 50-500 $g/m^2$, such as 100-400 $g/m^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°. Suitably, the further absorbent layer or layers are substantially coextensive with the absorbent layer according to the invention.

The wound facing surface of the dressing is suitably protected by a removable cover sheet. The cover sheet is normally formed from flexible thermoplastic material. Suitable materials include polyesters and polyolefins. Suitably, the adhesive-facing surface of the cover sheet is a release surface. That is to say, a surface that is only weakly adherent to the absorbent layers and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the present invention is sterile and packaged in a microorganism-impermeable container.

In a further aspect, the present invention provides method of treatment of a wound comprising applying thereto an effective amount of a dressing material according to the present invention. Suitably, the treatment comprises applying to said wound a dressing according to the present invention.

The material is suitably applied to the wound for a period of at least about 1 hour, more suitably from about 4 hours to about 4 weeks, for example from about 1 day to about 14 days, optionally with dressing changes during the course of the treatment.

In a further aspect, the present invention provides a method of making a porous wound dressing material comprising the steps of providing a substrate of a solid hydrophilic first foam material; applying a fluid or gel polyurethane foam prepolymer mixture to at least one surface of said solid substrate; and curing said prepolymer in contact with said solid substrate.

Various alternative procedures are possible, depending on the desired degree of impregnation of the polyurethane prepolymer into the substrate.

The solid substrate is suitably in the form of a sheet. In certain embodiments, a layer of the prepolymer mixture is cast onto a release sheet and the solid substrate is laid on top of prepolymer before curing so that at least a portion of the prepolymer impregnates at least the surface pores of the substrate. Pressure may be applied to assist uptake of the prepolymer into the substrate. The prepolymer is then cured and dried in contact with the substrate and the release sheet.

In other embodiments, a layer of the prepolymer mixture is cast onto a surface of the substrate so that at least a portion of the prepolymer impregnates at least the surface pores of the substrate. The prepolymer is then cured and dried in contact with the substrate.

In other embodiments, the substrate is compressed and released in the presence of the prepolymer mixture, for example by passing the substrate through a nip roller with the prepolymer mixture, followed by curing and drying. The degree of impregnation can be controlled by the amount of compression and the amount of the prepolymer, for example by varying the spacing of the nip roller.

In other embodiments, a layer of the prepolymer mixture is cast onto a release sheet and the solid substrate impregnated with a suitable solvent such as water is laid on top of prepolymer before curing to assist migration of the prepolymer into the substrate. The prepolymer is then cured and dried in contact with the substrate and the release sheet.

As previously noted, the polyurethane prepolymer mixture comprises diisocyanates or isocyanate-capped prepolymers with suitable chain extending compounds having amine and/or alcohol multiple functionality. Suitably, the isocyanate-capped prepolymer comprises from 0.5 to 1.2 meq NCO groups/g. Suitably, the isocyanate-capped prepolymer is an isocyanate-capped polyether prepolymer. More suitably, the prepolymer is an isocyanate-capped oxy ethylene oxy/propylene copolymer. Suitable prepolymers are available under the Registered Trade Mark HYPOL from Dow Chemical Company.

The mixture further comprises a polyurethane or polyurea chain terminating compound, suitably selected from monohydric alcohols such as C1 to C3 alcohols, and amines, for example a mixture of mono-amines and diamines. The amounts of chain extending and terminating compounds influence the physical properties of the foam. In particular, aminediamine chain terminating/extending compounds react with the prepolymer very much faster than water and methanol. For example, the tackiness of the foam increases with increasing monohydric alcohol or monoamine content in the aqueous layer. Suitably, the chain extending and terminating compounds are present in the prepolymer in an amount of 0.05 to 0.4 parts for alcohols and 0.01 to 0.05 parts for the amines, based on one part by weight of the isocyanate prepolymer.

In certain embodiments, the aqueous layer further comprises a catalyst for the polymerisation, suitably a diamine such as diazobicyclo octane or dimethylaminoethyl ether. Suitably, the catalysts are present in the prepolymer mixture in an amount of 0.002 to 0.05 parts by weight, based on one part by weight of the isocyanate prepolymer.

Suitably, the fluid or gel prepolymer mixture comprises water, which reacts with the isocyanate residues to release $CO_2$ for foaming. The amount of water in the mixture is suitably about 0.4 to about 1.0 parts by weight of water per one part of the isocyanate prepolymer.

Accordingly, the fluid or gel prepolymer mixture for use in the method of the invention suitably comprises: 1 part by weight of an isocyanate-capped prepolymer having from about 0.5 to about 1.2 meq NCO groups/g; from about 0.4 to about 1.0 parts by weight of water; and from about 0.05 to about 0.4 parts by weight of a C1 to C3 monohydric alcohol.

Although the above embodiments comprise a C1-C3 alcohol, i.e. any of methanol, ethanol or propanol, the use of methanol is particularly preferred. All three alcohols reduce the rate of reaction between the isocyanate-capped prepolymer and water, but the effect of methanol is more marked. A reduction of the reaction rate is desirable in order to facilitate mixing of the various components and spreading of the reaction mixture into the substrate.

The isocyanate prepolymer mixture may comprise other conventional wound therapeutic materials. Suitable therapeutic materials include: antiseptics such as molecular silver, silver sulfadiazine or chlorhexidine; pain relieving agents such as lignocaine; anti-scarring agents such as mannose-6-phosphate, and agents for promoting wound healing such as growth factors. Alternatively or additionally, the wound therapeutic materials may be applied to the material after curing of the polyurethane foam, for example by applying a dispersion of the therapeutic materials in a suitable solvent followed by drying as described in WO-A-2005075001.

The viscosity of the prepolymer fluid can be controlled by adding an inert solvent, such as tetrahydrofuran, as a diluent.

It will be appreciated that other components may be added to the reaction mixture in the method of the invention, in order to give desired properties to the product. In particular, it is preferable to include a small proportion (e.g. up to 30% by weight of the wet composition) of a rubber, which may be either natural or synthetic. This has the effect of increasing the cure time for the polyurethane, and increases extensibility, strength and tack. Most importantly, it substantially reduces shrinkage of the gel on drying, and it also improves bubble formation, producing more regular, smaller bubbles.

In addition to the methanol or ethanol, other alcohols, and particularly polyols, may be included in the reaction mixture to produce a softer, more conformable foam. For example, a polyol sold by Bayer AG under the Trade Mark LEVAGEL may be used. However, traces of such alcohols are likely to remain in the free form after the foaming reaction, and these traces may be difficult to remove from the foam merely by heating. The use of higher boiling alcohols is therefore suitably avoided if the foam is to be used as a wound contact layer, because of the likelihood that such alcohols will be leached from the foam during use of the dressing. When used as or in wound dressings, the foams of the invention suitably contain less than 1% by weight of water soluble alcohols, and more suitably less than 0.1% by weight. It is particularly preferred that the foams of the invention are essentially free of water soluble alcohols (eg. less than 0.01% by weight).

Suitably, the curing of the prepolymer mixture is carried out at ambient temperatures, i.e. 15 to 25° C. Suitably, for monohydric alcohol systems, the mixture is cured for 5 to 100 minutes, suitably to 20 minutes. Suitably, for systems containing diamines, the layers are cured for 0.5 to 10 minutes, more suitably for 1 to 3 minutes.

Suitably, the process according to the present invention further comprises drying the polyurethane foam, for example at a temperature of from about 35° C. to about 60° C. Suitably, the water content of the product foam is less than about 1% by weight. The process may further comprise sterilizing the resulting material, for example with gamma irradiation.

Suitably, the method of the present invention may be used to make a wound dressing material according to the invention.

Any feature that has been described above in relation to any one aspect of the invention is also suitable in conjunction with any other embodiment without limitation.

Specific embodiments of the invention will now be described further, by way of example, with reference to the accompanying drawings, in which.

Figure 1:
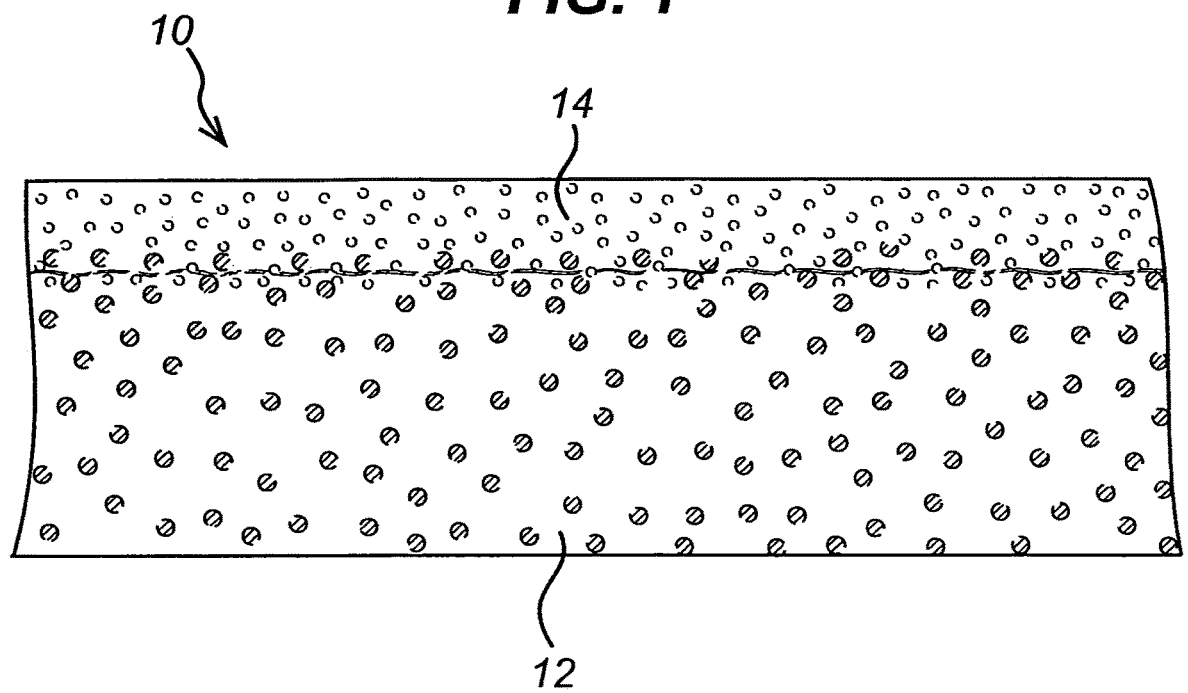
FIG. 1 shows a cross-sectional view through a portion of a first wound dressing sheet material according to the present invention.

Referring to FIG. 1, the wound dressing material 10 according to the present invention comprises a substrate (support) layer 12 of open-cell hydrophilic polyurethane foam, and a wound-contacting layer 14 of hydrophilic polyurethane foam that has been formed by applying a layer of fluid foaming prepolymer to the surface of the substrate layer, and allowing the prepolymer to be penetrate partially into the substrate foam before and during curing in situ.

Figure 2:
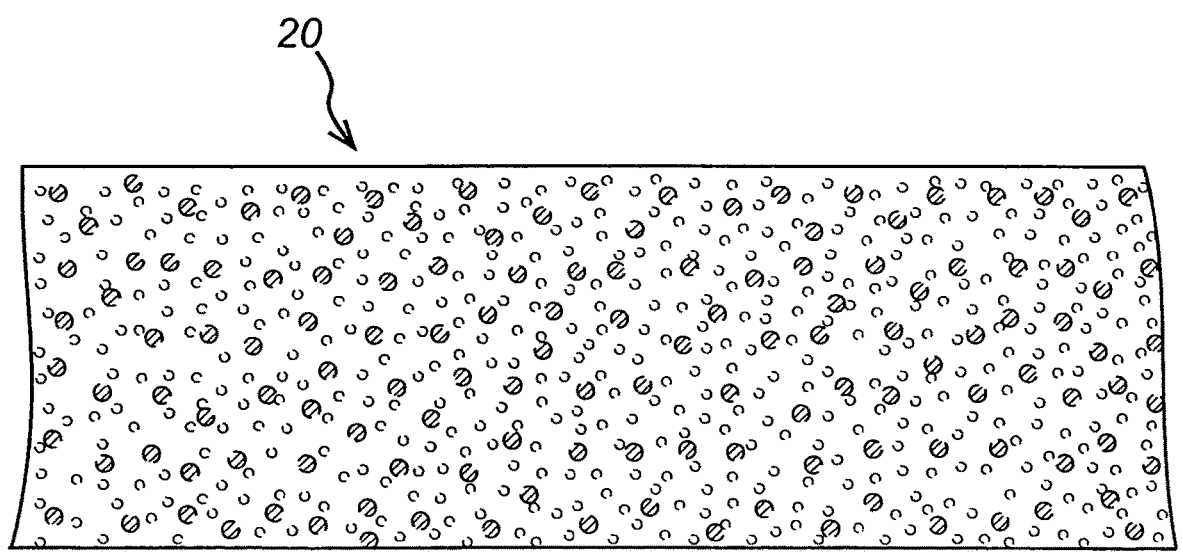
FIG. 2 shows a cross-sectional view through a portion of a second wound dressing sheet material according to the present invention.

Referring to FIG. 2, the wound dressing material 20 according to this embodiment of the present invention comprises a substrate (support) layer of open-cell hydrophilic polyurethane foam, that is uniformly impregnated with a hydrophilic polyurethane foam by applying the support layer to a layer of fluid foaming prepolymer on a release surface, followed by compressing the support layer with a roller to impregnate the prepolymer mixture into the support layer prior to curing and drying.

Figure 3:
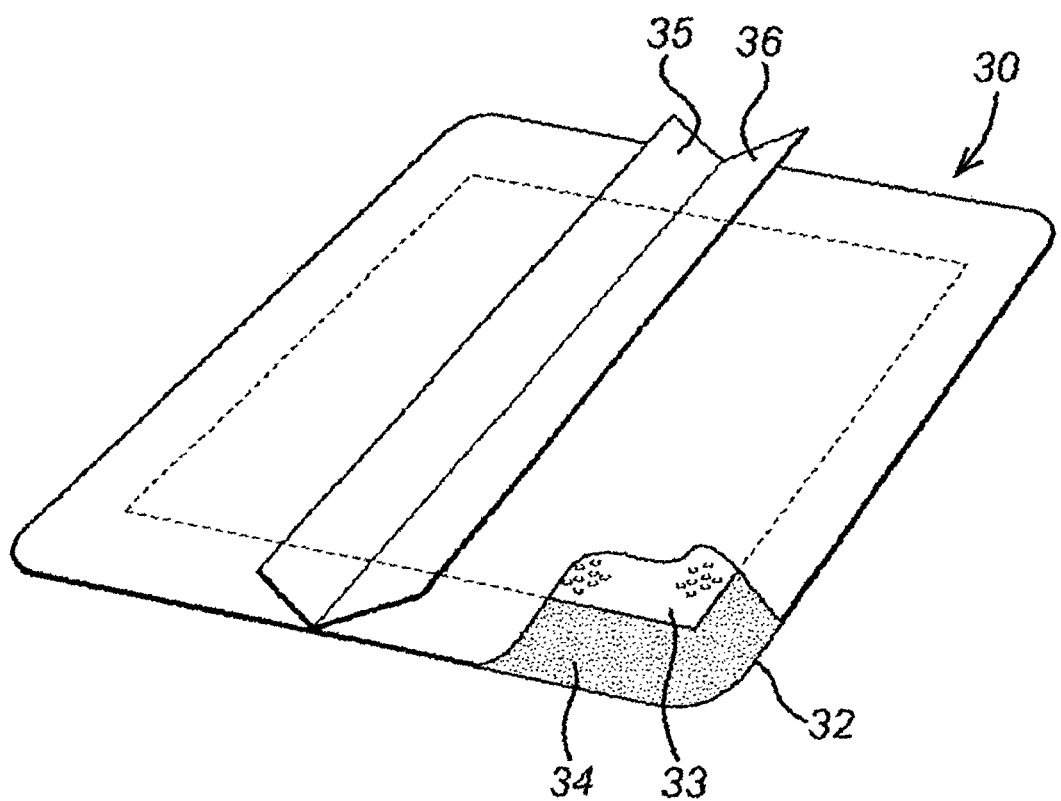
FIG. 3 shows a wound dressing according to the present invention incorporating a sheet of the material according to the invention.

Referring to FIG. 3, the wound dressing 30 according to the present invention is an island-type, self-adhesive wound dressing comprising a backing layer 32 of microporous liquid-impermeable polyurethane foam. The backing layer 32 is permeable to water vapor, but impermeable to wound exudate and microorganisms.

The backing layer is coated with a substantially continuous layer of pressure-sensitive polyurethane adhesive. A rectangular island 33 of a wound dressing material according to the invention in sheet form, made in accordance with Example 1 below, is adhered to a central region of the adhesive-coated backing sheet 32 such that an adhesive-coated margin 34 of the backing sheet extends around the island for attachment of the dressing to the skin around a wound. The dressing further comprises protective, release-coated cover sheets 35,36. These cover sheets are removed immediately before use of the dressing. The dressing is suitably sterile and packaged in a microorganism-impermeable pouch (not shown) prior to use.

Wound dressing materials according to the invention were prepared using the following foam substrate (support) layers and polyurethane foam prepolymer:

Substrate 1: Open-cell hydrophilic polyurethane foam, density 27 kg/m³, cell count 24 per cm, tensile strength 150 kPa, 50% compression set less than 10%, uncompressed thickness 2 mm, manufactured by VITA, supplied by Caligen Foam Limited, Foam Grade XD4100AS;

Substrate 2: Open-cell hydrophilic polyurethane foam, density 27 kg/m³, cell count 16 per cm; tensile strength greater than 100 kPa, uncompressed thickness 2.5 mm, manufactured by Tramico, Foam Grade S2923P;

Fluid Prepolymer: mixture of 50% HYPOL prepolymer, 3% methanol, 16% water and 6% acrylic adhesive.

Example 1

The prepolymer was mixed and spread 0.5 mm thick on a release paper and before the prepolymer cured, a piece (5 cm×5 cm) of Substrate foam 1 was placed onto the prepolymer so that the prepolymer could penetrate and bond to the surface of the substrate. The resulting laminate was then placed in an oven to dry. The basis weight of the prepolymer mixture was 0.74 g/5 cm×5 cm.

Example 2

The procedure of Example 1 was repeated with replacement of Substrate foam 1 by Substrate foam 2. The basis weight of the prepolymer mixture was 0.48 g/5 cm×5 cm.

Example 3

The prepolymer was mixed and spread 0.5 mm thick on a release paper and before the prepolymer cured, a piece (5 cm×5 cm) of Substrate foam 1 was placed onto the prepolymer and a roller was used to squeeze the prepolymer mixture completely through the substrate. The resulting impregnated substrate was then placed in an oven to dry. The basis weight of the prepolymer mixture was 0.49 g/5 cm×5 cm.

Example 4

The procedure of Example 3 was repeated with replacement of Substrate foam 1 by Substrate foam 2. The basis weight of the prepolymer mixture was 0.80 g/5 cm×5 cm.

Reference Example 5

A reference material consisting only of the hydrophilic polyurethane foam material was prepared by mixing and spreading the prepolymer 0.5 mm thick on a release paper, allowing it to cure at ambient temperature, followed by drying in an oven.

Procedure 1: Absorbency Measurement

The method consists of placing a pre-weighed sample into a galvanised steel wire basket, the basket is then completely submerged in 0.9% saline solution for 15 minutes. The basket and sample are then drained for 15 seconds, and the sample is then re-weighed. Subtracting the initial weight from the final weight gives the quantity of fluid absorbed. The percentage increase in thickness of the sheet due to water absorption was also measured. The results are given in Table 1 (standard deviations given in parentheses).

TABLE 1

|  | Absorbency g/cm² | % Increase size | % Increase Absorbency |
| --- | --- | --- | --- |
| Substrate 1 | 0.06 (0.01) | 0 | N/A |
| Example 1 | 0.21 (001) | 83.54 (1.95) | 247.54 |
| Substrate 2 | 0.13 (0.03) | 0 | N/A |
| Example 2 | 0.37 (0.02) | 65.50 (2.9) | 187.60 |
| Example 3 | 0.16 (0.01) | 24.67 (2.54) | 154.10 |
| Example 4 | 0.25 (0.01) | 46.4 (6.79) | 89.92 |
| Reference Example 5 | 0.35 (0.06) | 189.0 (0.03) | N/A |

It can readily be seen from these data that the hydrophilic polyurethane foam layer greatly increases the liquid absorbency of the foam substrates. However, the overall swelling in water of the materials of the invention is still substantially less than that of the pure polyurethane foam reference example 5.

Procedure 2: Tensile Strength Measurement

Samples of the material were cut with dimension 5 cm×2.5 cm. These are then evaluated using an INSTRON (registered trade mark) tensile tester, where the maximum load and extension at break are recorded. For the Wet tensile test the samples are submerged in 0.9% saline solution for 15 minutes prior to evaluation.

TABLE 2

|  | Maximum load(gf) | | % Extension break | |
| --- | --- | --- | --- | --- |
|  | DRY | WET | DRY | WET |
| Substrate 1 | 1245 (62) | 799 (74) | 368 (34) | 309 (32) |
| Example 1 | 1391 (203) | 806 (70) | 337 (74) | 159 (19) |
| Substrate 2 | 734 (50) | 524 (42) | 174 (10) | 170 (17) |
| Example 2 | 1007 (84) | 445 (58) | 236 (17) | 170 (5) |
| Reference Example 5 | 690 (30) | 160 (17) | 847 (47) | 109 (29) |

It can readily be seen from these data that the materials according to the invention have substantially greater wet strength and lower deformation when wet as compared to the pure hydropolymer foam reference Example 5. This translates into greater mechanical strength of the materials in use. A further advantage is that the support layer provides increased cushioning of the wound as compared to the pure polyurethane foam layer of Reference Example 5

All patent applications referred to herein are expressly incorporated in their entirety.

The above examples have been described for the purpose of illustration only. Many other embodiments falling within the scope of the accompanying claims will be apparent to the skilled reader.

The invention claimed is:

1. A wound dressing material, comprising:
   a solid substrate having a plurality of interconnected interstitial spaces therein, wherein said solid substrate is a hydrophilic open-cell foam material; and
   a hydrophilic polyurethane foam forms a substantially continuous interstitial foam structure extending between the plurality of interconnected interstitial spaces of said solid substrate.

2. The wound dressing material of claim 1, wherein said hydrophilic polyurethane foam is applied to one side only of said solid substrate.

3. The wound dressing material of claim 2, wherein one surface of said wound dressing material consists essentially of said hydrophilic polyurethane foam.

4. A wound dressing comprising the wound dressing material of claim 1.

5. The wound dressing of claim 4 which is sterile and packaged in a microorganism-impermeable container.

6. The wound dressing material of claim 1, wherein said solid substrate is elastically compressible and exhibits an elongation at break of at least about 100%.

7. The wound dressing material of claim 1, comprising from about 10 wt % to about 90 wt % of said hydrophilic polyurethane foam, based on total weight of the wound dressing material.

8. The wound dressing material of claim 1, wherein said hydrophilic polyurethane foam has a basis weight of from about 0.2 to about 1.5 kg/m2.

9. The wound dressing material of claim 1, wherein the interstitial spaces are present in the solid substrate at from about 5 to about 30 pores per cm.

10. A method of making a porous wound dressing material comprising the steps of:
    providing a substrate of a solid hydrophilic first foam material having a plurality of interconnected interstitial spaces therein;
    applying a fluid or gel polyurethane foam prepolymer mixture to at least one surface of said substrate such that the fluid or gel polyurethane foam prepolymer mixture is distributed within the plurality of interconnected interstitial spaces of said substrate; and
    curing said fluid or gel polyurethane foam prepolymer mixture to provide a hydrophilic polyurethane foam that forms a substantially continuous interstitial foam structure extending between the plurality of interconnected interstitial spaces of said substrate.

11. The method of claim 10, wherein the fluid or gel polyurethane foam prepolymer mixture comprises: 1 part by weight of an isocyanate-capped prepolymer having from about 0.5 to about 1.2 meq NCO groups/g; from about 0.4 to about 1.0 parts by weight of water; and from about 0.05 to about 0.4 parts by weight of a C1 to C3 monohydric alcohol.

12. The method of claim 10, wherein said step of applying comprises compressing and releasing said substrate in contact with said fluid or gel polyurethane foam prepolymer mixture to increase uptake of the fluid or gel polyurethane foam prepolymer mixture into the substrate.

13. The method of claim 10, wherein said step of applying comprises: applying a solvent to said substrate, applying a layer of said fluid or gel polyurethane foam prepolymer mixture to said substrate, and allowing the fluid or gel polyurethane foam prepolymer mixture to impregnate the substrate.

14. The method of claim 10 further comprising sterilizing said wound dressing material.

15. The wound dressing material of claim 10, wherein the interstitial spaces are present in the substrate at from about 5 to about 30 pores per cm.

16. A wound dressing material formed by a method comprising:
    providing a substrate of a solid hydrophilic first foam material having a plurality of interconnected interstitial spaces therein;
    applying a fluid or gel polyurethane foam prepolymer mixture to at least one surface of said substrate such that the fluid or gel polyurethane foam prepolymer mixture is distributed within the plurality of interconnected interstitial spaces of said substrate; and
    curing said fluid or gel polyurethane foam prepolymer mixture to provide a hydrophilic polyurethane foam that forms a substantially continuous interstitial foam structure extending between the plurality of interconnected interstitial spaces of said substrate.

17. The wound dressing material of claim 16, wherein the fluid or gel polyurethane foam prepolymer mixture comprises: 1 part by weight of an isocyanate-capped prepolymer having from about 0.5 to about 1.2 meq NCO groups/g; from about 0.4 to about 1.0 parts by weight of water; and from about 0.05 to about 0.4 parts by weight of a C1 to C3 monohydric alcohol.

18. The wound dressing material of claim 16, wherein said step of applying comprises compressing and releasing said substrate in contact with said fluid or gel polyurethane foam prepolymer mixture to increase uptake of the fluid or gel polyurethane foam prepolymer mixture into the substrate.

19. The wound dressing material of claim 16, wherein said step of applying comprises: applying a solvent to said substrate, applying a layer of said fluid or gel polyurethane foam prepolymer mixture to said substrate, and allowing the fluid or gel polyurethane foam prepolymer mixture to impregnate the substrate.

20. The wound dressing material of claim 10, wherein the interstitial spaces are present in the substrate at from about 5 to about 30 pores per cm.

* * * * *